United States Patent [19]

Butler et al.

[11] Patent Number: 4,758,585

[45] Date of Patent: Jul. 19, 1988

[54] SATURATED CYCLOALKYL (B) PYRROL-1 (2H)- ACETIC ACID AMIDES AND DERIVATIVES THEREOF

[75] Inventors: Donald E. Butler; John G. Topliss, both of Ann Arbor, Mich.

[73] Assignee: Warner-Lambert Company, Morris Plains, N.J.

[21] Appl. No.: 766,386

[22] Filed: Aug. 16, 1985

[51] Int. Cl.[4] .................... C07D 401/12; A61K 31/40
[52] U.S. Cl. .................................. 514/412; 514/323; 548/512; 546/208
[58] Field of Search ................ 548/512; 514/323, 412; 546/208

[56] References Cited

U.S. PATENT DOCUMENTS 4,337,265  6/1982  Treasuryuala ...................... 548/512
4,476,308  10/1984  Aschwanden et al. ............. 546/208
4,621,097  11/1986  Butler et al. ........................ 548/512

*Primary Examiner*—Nicholas S. Rizzo
*Attorney, Agent, or Firm*—Elizabeth M. Anderson

[57] ABSTRACT

A unique series of saturated cycloalkyl[b]pyrrol-1(2H)-acetic acid amides are useful as agents for the reversal of amnesia. Intermediates for preparing the compounds, pharmaceutical composition containing the compounds, and method for using the pharmaceutical compositions for treating senility and for the reversal of amnesia are described.

28 Claims, No Drawings

SATURATED CYCLOALKYL (B) PYRROL-1 (2H)-ACETIC ACID AMIDES AND DERIVATIVES THEREOFpg,

BACKGROUND OF THE INVENTION

The compounds of the instant invention are a series of saturated cycloalkyl[b]pyrrol-1(2H)-acetic acid amides useful for the treatment of senility and the reversal of amnesia.

A synthesis of cis-hexahydro-2-oxo-1(2H)cyclopenta[b]pyrrole is described in J. Chem. Soc., 1959, 1050–1054. A synthesis of cis-hexahydro-2-oxo-1(2H)-cyclohexa[b]pyrrole is described in Chem. Abstr. 62, 6452F, 1965. A synthesis of trans-hexahydro-2-oxo-1(2H)cyclohexa[b]pyrrole is described in (J. Chem. Soc., 1958, 2688-2693).

SUMMARY OF THE INVENTION

One aspect of the present invention is a generic compound having the structural formula

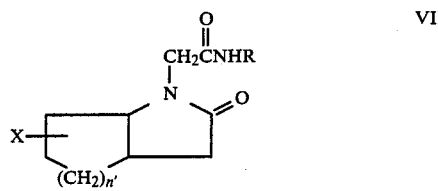

VII wherein n' is one, two, three, or four; X is H or a straight or branched alkyl of from one to four carbon atoms; and R is H or $(CH_2)_nN(R'R'')$ in which n is two or three and R' and R'' are each independently hydrogen or a straight or branched alkyl of from one to six carbon atoms, or combined with the nitrogen to which they are attached form a five to seven-member ring which may optionally be substituted with one or more alkyl groups of from one to four carbon atoms or a pharmaceutically acceptable acid addition salt of the compound containing a basic amine.

Another aspect of the present invention is a method of preparing a compound of Formula VII which comprises:

(a) reacting a 2-carboalkoxycycloalkanone with an alkali metal hydride and an alkyl α-haloacetate to form, (b) a 2-carboalkoxy-2-carboalkoxymethylcycloalkanone which is then reacted with acid to form the cycloalkanone-2-acetic acid which is then, (c) converted by reaction with an alcohol in the presence of acid to form, (d) the corresponding cycloalkanone-2-acetic acid alkyl ester which is then, (e) treated with O-methylhydroxylamine hydrochloride to form the corresponding cycloalkanone-2acetic acid alkylester o-methyloxime which, (f) is then hydrogenated in the presence of a catalyst to form the corresponding 2-oxo-cycloalkyl-[b]pyrrole, (g) this is then reacted with an alkali metal hydride and an alkyl-α-haloacetate to form the corresponding 2-oxo-cyloalkyl[b]pyrrole acetic acid alkyl ester which is then, (h) reacted with ammonia or a primary amine to form saturated cycloalkyl[b]pyrrole acetic acid amides.

A third aspect of the present invention is a second method of preparing a compound of Formula VII which comprises:

(a) preparing a p-alkylglyoxylanilide by known methods from the corresponding p-alkyl aniline and then, (b) reacting the glyoxylanilide with an acid to produce the corresponding 5-alkyl-2,3-dioxo-indole which is then, (c) catalytically hydrogenated to form the corresponding 5-alkyl-2-oxo-indole which is then, (d) treated with an alkali metal hydride and an alkyl α-halo-acetate to form the 5-alkyl-2-oxo-indole acetic acid ester which is, (e) treated with ammonia or a primary amine to form 5-alkyl-2-oxo-indole-acetic acid amide.

A fourth aspect of the present invention is a pharmaceutical composition which comprises an effective amount of a compound of structural Formula VII above in combination with a pharmaceutically acceptable carrier.

A fifth aspect of the present invention is a method of treating senility in a mammal comprising administering to a mammal an effective amount of the above identified pharmaceutical composition.

A sixth aspect of the present invention is a method of reversing amnesia in a mammal comprising administering to the mammal an effective amount of the above identified pharmaceutical composition.

DETAILED DESCRIPTION

Compounds of the formula:

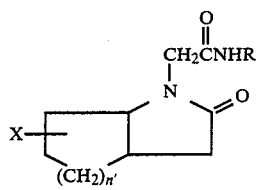

VII may be prepared by the following schematic procedures.

SCHEME I

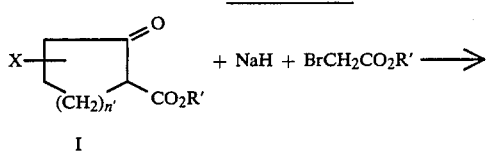

I

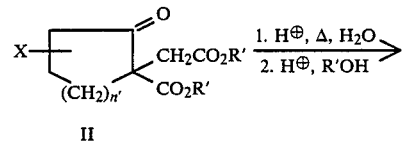

II

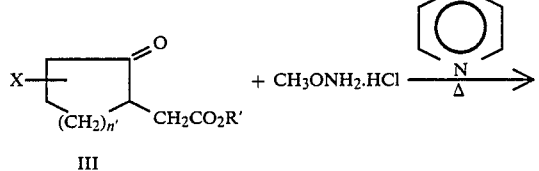

III

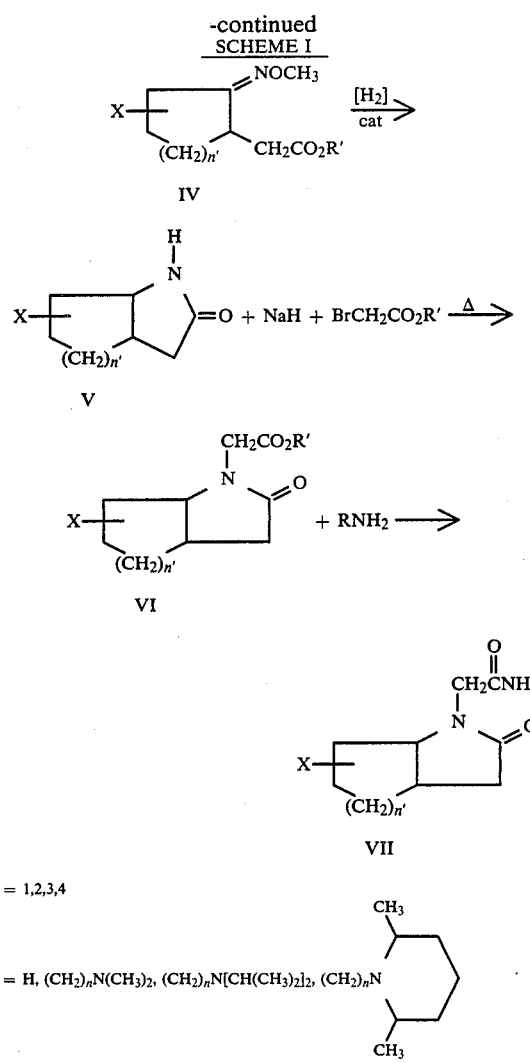

n' = 1,2,3,4

R = H, (CH$_2$)$_n$N(CH$_3$)$_2$, (CH$_2$)$_n$N[CH(CH$_3$)$_2$]$_2$, (CH$_2$)$_n$N⟨(CH$_3$)(CH$_3$) cyclohexyl⟩ n = 2,3
R' = CH$_3$ or C$_2$H$_5$
X = H or an alkyl group of from 1-4 carbon atoms.
n" = 0,1,2,3

For example, the preparation of representative preferred embodiment of the cis- and trans-isomers of the compounds is as follows.

2-Carboalkoxy-cycloalkanone (I) is treated with sodium hydride and an alkyl α-bromoacetate to from the corresponding 2-carboalkoxy-2-carboalkoxymethylcycloalkanone (II).

For example, a solution of 2-carboethoxy-cycloheptanone (I) (92.2 g, 0.5 mole) in toluene (1.6 l) is treated with sodium iodide (1 g) and 60% sodium hydride in mineral oil (23.3 g, 0.58 mole). The mixture is heated at 110° C. until hydrogen gas evolution drops off. Ethyl bromoacetate (98.0 g, 0.58 mole) is added dropwise and the mixture is warmed to 65° C. for 18 hours. The mixture is cooled and water (500 ml) is added. The layers are separated and the aqueous layer is extracted with toluene (2×1 l). The extracts are dried (MgSO$_4$) and filtered. The filtrate is concentrated at reduced pressure and distilled to yield pure 2-carboethoxy-2-carboethoxymethylcycloheptanone (II) with a bp 182°-185° C. at 13 mm.

A solution of 2-carboethoxy-cyclooctanone (92.2 g, 0.5 mole) in toluene (1.6 l) is treated with sodium iodide (1 g) and 60% sodium hydride in mineral oil (23.3 g, 0.58 mole). The mixture is heated at 110° C. The mixture is treated with ethyl α-bromoacetate (98.0 g, 0.58 mole) dropwise and the mixture is warmed to 65° C. for 18 hours. The mixture is cooled and water (500 ml) was added. The layers are separated and the aqueous is extracted with toluene (2×1 l). The extracts are dried (MgSO$_4$) and filtered. The filtrate is concentrated at reduced pressure and distilled to yield pure 2-carboethoxy-2-carboethoxymethylcyclooctanone with a bp of 193°-195° C. at 16 mm.

Next the 2-carboalkoxy-2-carboalkoxymethyl cycloalkanone is stirred and heated with aqueous acid at reflux to yield the cycloalkanone-2-acetic acids which are used crude.

For example, a mixture of 2-carboethoxy-2-carboethoxymethylcycloheptanone (27 g, 0.1 mole) and concentrated hydrochloric acid (75 ml) is stirred and refluxed for three hours. At this point a further addition of concentrated hydrochloric acid (50 ml) is made and reflux is continued for three hours. The solution is concentrated in vacuo and the residue is extracted with chloroform (2×250 ml). The combined extracts are dried (MgSO$_4$) filtered, concentrated in vacuo, and the cycloheptanone-2-acetic acid used as such.

Another example is, a suspension of 2-carboethoxy-2-carboethoxymethylcyclooctanone (73.5 g, 0.26 mole) in concentrated hydrochloric acid is stirred and refluxed for six hours. The mixture is concentrated in vacuo and treated with fresh concentrated hydrochloric acid and refluxed for three hours. The mixture is concentrated in vacuo and partitioned between excess aqueous sodium bicarbonate and diethylether. The aqueous layer is acidified with excess concentrated hydrochloric acid to yield an oil. The viscous oil crystallizes on standing and recrystallization from diethyl ether-pentane yields cyclooctanone-2-acetic acid with mp 73°-5° C.

Next a solution of the cycloalkanone-2-acetic acid is dissolved in alcohol and catalytically esterified to the cycloalkanone-2-acetic acid alkyl ester (III).

For example, a solution of cycloheptanone-2-acetic acid (42.5 g, 0.25 mole) is dissolved in methanol (250 ml) and the solution is saturated with hydrogen chloride gas. The solution is refluxed 18 hours, cooled, concentrated, and distilled to yield pure cycloheptanone-2-acetic acid methyl ester with bp 136°-139° C. at 13 mm.

Another example is, a solution of cyclootanone-2-acetic acid (61.9 g, 0.336 mole) is dissolved in methanol (250 ml) and the solution is saturated with hydrogen chloride gas. The solution refluxed 18 hours, cooled, concentrated, and distilled to yield pure cyclooctanone-2-acetic acid methyl ester with a bp 156°-159° C. at 13 mm.

Next a solution of the cycloalkanone-2-acetic acid alkyl ester is dissolved in pyridine and treated with O-methylhydroxylamine.hydrochloride to form the corresponding cycloalkanone-2-acetic alkyl ester O-methyloxime (IV).

For example, a solution of cycloheptanone-2-acetic acid methyl ester (III) (38.0 g, 0.2 mol) in pyridine (400 ml) under a N$_2$ atmosphere is treated with O-methylhydroxylamine.hydrochloride (20 g, 0.24 mole). The mixture is stirred for 72 hours and is poured into water (800 ml). The turbid mixture is extracted with chloroform (5×250 ml). The combined extracts are dried (MgSO$_4$), filtered, concentrated, and distilled to yield pure cycloheptanone-2-acetic acid methyl ester O-methyloxime IV with a bp 128°-129° C. at 16 mm.

Another example of this step is a solution of cyclooctanone-2-acetic acid methyl ester (III) (39.6 g, 0.2 mole) in pyridine (400 ml) under a N₂ atmosphere is treated with O-methylhydroxyamine.hydrochloride (20 g, 0.24 mole). The mixture is stirred for 72 hours and is poured into water (800 ml). The turbid mixture is extracted with chloroform (5×250 ml). The combined extracts are dried (MgSO₄), filtered, concentrated, and distilled to yield pure cyclooctanone-2-acetic acid methyl ester O-methyloxime (IV) with a bp 142°–143° C. at 19 mm.

A cycloalkanone-2-acetic acid alkyl ester O-methyloxime (IV) is hydrogenated in the presence of a catalyst to form the corresponding isomer of 2-oxo-1(2H)-cycloalkyl[b]pyrrole.

For example a solution of cycloheptanone-2-acetic acid methyl ester O-methyloxime IV (33 g, 0.15 mole) in methanol (330 ml) is treated with hydrogen gas in the presence of 20% Pd/C (1 g) at 50° C. The suspension is filtered and concentrated at reduced pressure to yield crude cis-octahydro-2-oxo-1(2H)cyclohepta[b]pyrrole. Distillation yields pure cis-octahydro-2-oxo-1(2H)-cyclohepta[b]pyrrole (V) with a bp 113°–115° C. at 0.1 mm and a mp 70°–73° C. after recrystallization from cyclohexane.

Another example of this step is a solution of cyclooctanone-2-acetic acid methyl ester O-methyloxime (IV) (33 g, 0.147 mole) in methanol (350 ml) is treated with hydrogen gas in the presence of 5% Rh/C (1 g) at 50° C. The suspension is filtered and concentrated at reduced pressure to yield crude cis-oxtahydro-2-oxo-1(2H)cycloocta[b]pyrrole (V). Crystallization from anhydrous diethyl ether yields pure cis-octahydro-2-oxo-1(2H)cycloocta[b]pyrrole (V) with a mp 75°–80° C.

A 2-oxo-1(2H)cycloalkyl[b]pyrrole is reacted with sodium hydride and an alkyl α-bromoacetate to from the corresponding 2-oxo-cycloalkyl[b]pyrrole-1(2H)-acetic acid alkyl ester (VI).

For example a solution of cis-hexahydro-2-oxo-1(2H)cyclopenta[b]pyrrole (V) (18.52 g, 0.148 mole) in tetrahydrofuran (200 ml) is treated with 50% sodium hydride in mineral oil (4.32 g, 0.18 mole) prewashed with toluene (3×100 ml). The mixture is stirred 30 minutes and treated with ethyl α-bromoacetate (34.6 g, 0.1856 mole). The mixture is stirred and heated at 45°–50° C. for 2, 5, and 18 hours at ambient temperature. The suspension is filtered through filteraid. The solution is concentrated at reduced pressure and distilled to yield an oil. Chromatography over silica gel (elution with dichloromethane and methanol, 97.5 and 2.5, respectively), concentration of the eluate and distillation yields pure cis-hexahydro-2-oxo-cyclopenta[b]pyrrole-1(2H)acetic acid ethyl ester (VI) with bp 113°–115° C. at 0.35 mm.

A second example of this step is a solution of cis-hexahydro-2-oxo-1(2H)cyclohexa[b]pyrrole (V) (69.6 g, 0.50 mole) in tetrahydrofuran (200 ml) is treated with 50% sodium hydride in mineral oil (13.2 g, 0.55 mole) prewashed with toluene (3×100 ml). The mixture is stirred at reflux for one hour and treated with ethyl α-bromoacetate (91.9 g, 0.55 mole). The mixture is stirred at reflux for one hour and treated with 50% sodium hydride in mineral oil (1.2 g, 0.05 mole), prewashed with toluene (3×100 ml) and ethyl α-bromoacetate (8.26 g, 0.05 mole). The mixture is refluxed one hour. Water (10 ml) is added. The suspension is filtered through filteraid. The solution is concentrated at reduced pressure and distilled to yield an oil. Chromatography over silica gel (elution with dichloromethane; methanol, 99-1), concentration of the eluate and distillation yields pure cis-hexahydro-2-oxo-cyclohexa[b]pyrrol-1(2H)-acetic acid ethyl ester also known as cis-octahydro-2-oxo-1H-indole-acetic acid ethyl ester (VI) with bp 90°–92° C. at 0.075 mm.

A third example is a solution of trans-hexahydro-2-oxo-1(2H)cyclohexa[b]pyrrole (V) (69.6 g, 0.50 mole) in tetrahydrofuran (200 ml) is treated with 50% sodium hydride in mineral oil (13.2 g, 0.55 mole) prewashed with toluene (3×100 ml). The mixture is stirred at reflux for one hour and treated with ethyl α-bromoacetate (91.9 g, 0.55 mole). The mixture is stirred one hour and refluxed one hour. The mixture is cooled and treated with 50% sodium hydride in mineral oil (1.2 g, 0.05 mole) and ethyl α-bromoacetate (8.25 g, 0.05 mole). The mixture is refluxed one hour. Water (10 ml) is added. The suspension is filtered through filteraid. The solution is concentrated at reduced pressure and distilled to yield an oil. Chromatography over silica gel (elution with dichloromethane; methanol 99-1), concentration of the eluate and distillation yields pure trans-hexahydro-2-oxo-cyclohexa[b]pyrrol-1(2H)-acetic acid ethyl ester also known as trans-octahydro-2-oxo-1H-indole-1-acetic acid ethyl ester (VI).

A fourth example is a solution of cis-octahydro-2-oxo-1(2H)cyclohepta[b]pyrrole (V) (12.7 g, 0.08 mole) in tetrahydrofuran (200 ml)-toluene (200 ml) is treated with 60% sodium hydride (0.5 g, 0.085 mole) at reflux. The mixture is refluxed one hour and treated with ethyl α-bromoacetate (14.2 g, 0.085 mole) is added. The mixture is refluxed while the tetrahydrofuran is distilled. The mixture is refluxed 1.5 hours at 110° C. The solution is cooled, diluted with diethyl ether, and filtered. The solution is concentrated at reduced pressure and distilled to yield pure cis-octahydro-2-oxo-cyclohepta[b]pyrrole-1(2H)-acetic acid ethyl ester (VII) with bp 115°–117° C. at 0.1 mm.

A fifth example of this step is a solution of cis-decahydro-2-oxo-1(2H)cycloocta[b]pyrrole (V) (20.3 g, 0.121 mole) in tetrahydrofuran (200 ml)toluene (200 ml) is treated with 60% sodium hydride (5.5 g, 0.13 mole) at reflux. After one hour, the mixture is treated with ethyl α-bromoacetate (24.2 g, 0.15 mole). The mixture is refluxed while the tetrahydrofuran is distilled. The mixture is refluxed 1.5 hours at 110° C. The solution is cooled, diluted with diethyl ether, and filtered. The solution is concentrated at reduced pressure and washed with n-pentane. The oil is distilled to yield pure cis-decahydro-2-oxo-1H-cycloocta[b]pyrrole-1-acetic acid ethyl ester (VI) with bp 132°–133° C. at 0.06 mm.

A 2-oxo-cycloalkyl[b]pyrrole-1(2H)acetic acid alkyl ester is treated with ammonia or an amine to form the corresponding 2-oxo-cycloalkyl[b]pyrrole-1(2H)acetic acid amide.

A example of this step is a solution of cis-hexahydro-2-oxo-cyclopenta[b]pyrrole-1(2H)-acetic acid ethyl ester (3.25 g, 0.0154 mole) in methanol (200 ml) is saturated with anhydrous ammonia and stirred at ambient temperature 24 hours. The solution is concentrated at reduced pressure to yield a solid. Recrystallization from acetonitrile yields pure cis-hexahydro-2-oxo-cyclopenta[b]pyrrole-1(2H)acetamide with a mp 142.5°–143.5° C.

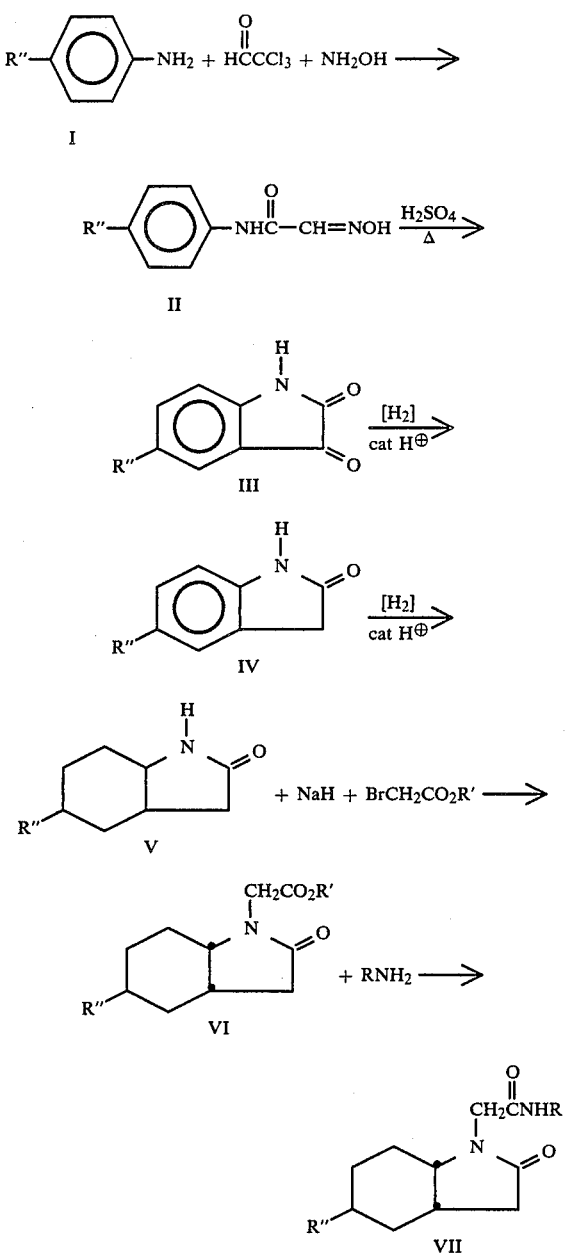

Scheme II

R, R', n as above;
R'' = H, CH₃, C₂H₅, n-C₄H₉—

For example, the preparation of representative preferred emodiment of the cis-isomers of the compounds is as follows.

A para-alkyl aniline (I) is treated with trichloroacetic acid and hydroxylamine to form para-alkyl glyoxylanilide (II). This is dissolved in concentrated sulfuric acid and heated to form 5-alkyl-octahydro-2,3-dioxo-1H-indole (III).

For example, a solution of 4-n-butylglyoxylanilide (II), (12.2 g, 0.01 mole) is added to concentrated sulfuric acid (23 ml) at 50° C. while maintaining the reaction mixture by cooling below 65° C. The mixture is held at 65° C. for one hour an poured unto ice with stirring. A reddish-orange precipitate is formed and is washed with water. Recrystallization from ethanol yields pure 5-n-butyl-octahydro-2,3-dioxo-1H-indole (III) with mp 112°-113° C.

A 5-alkyl-octahydro-2,3-dioxo-1H-indole is catalytically hydrogenated to form pure 5-alkyloctahydro-2-oxo-1H-indole (IV).

For example, a solution of 5-n-butyl-octahydro-2,3-dioxo-1H-indole (III) (43.6 g, 0.214 mole) in acetic acid (250 ml) is treated with hydrogen gas in the presence of 20% Pd/C (2 g). Another 1 g of 20% Pd/C is added and concentrated sulfuric acid (1 ml) is added and the hydrogenation is continued. Ten percent Rh/C (2 g) is added and hydrogenation is continued. The suspension is filtered and sodium acetate (4.9 g, 0.06 mole) is added and the mixture is concentrated at reduced pressure The residue is recrystallized from cyclohexane with the use of activated carbon to yield pure 5-n-butyloctahydro-2-oxo-1H-indole (V) with a mp 109°-111° C.

Reactions covering compounds IV to VII are explained in Scheme I.

An example is a solution of 5-n-butyl-octahydro-2-oxo-1H-indole (V) (22.24 g, 0.114 mole) in tetrahydrofuran (220 ml) is treated with 50% sodium hydride (2.88 g, 0.12 mole) prewashed with toluene (3×100 ml). The mixture is refluxed one hour and ethyl α-bromoacetate (20.94 g, 0.125 mole) is added. The mixture is refluxed one hour and diluted with diethyl ether. The suspension is filtered through filteraid. The solution is concentrated at reduced pressure to yield oil. The oil is chromatographed over silica gel (elution with dichloromethane and methanol, 99.5 and 0.5, respectively). The eluate is concentrated at reduced pressure and distilled to yield pure 5-n-butyloctahydro-2-oxo-1H-indole-acetic acid ethyl ester (3aα, 7aα) (VI) with bp 112°-115° C. at 0.07 mm.

A solution of 5-n-butyloctahydro-2-oxo-1H-indoleacetic acid ethyl ester (3aα, 7aα) (VI) (5.0 g, 0.0178 mole) in N,N-bis-(1-methylethyl)aminoethylamine (4.49 g, 0.0267 mole) is heated at 100° C. for 18 hours. The solution is concentrated at reduced pressure to an oil. The oil is dissolved in 2-propanol and the solution is treated with a saturated solution of hydrogen chloride in 2-propanol. The solution is diluted with anhydrous diethyl ether and allowed to crystallize. The crystals are filtered. Recrystalliztion from acetonitrile-diethyl ether yields pure 5-n-butyloctahydro-2-oxo-1H-indoleacetamide N-[bis[1-methylethyl]amino]ethyl]·hydrochloride (3aα, 7aα) (VII) with mp 116°-118° C.

For example, a solution of 5-n-butyloctahydro-2-oxo-1H-indole-acetic acid ethyl ester (3aα, 7aα) (5.0 g, 0.0179 mole) in methanol (50 ml) is saturated with anhydrous ammonia and stirred 18 hours at ambient temperature. The solution is concentrated at reduced pressure to yield a solid. Recrystallization from acetonitrile yields pure 5-n-butyloctahydro-2-1H-indole-acetamide (3α, 7aα)

For example, a solution of 5-n-butyloctahydro-2-oxo-1H-indole-acetic acid ethyl ester (3aα, 7aα) (5.0 g 0.0178 mole) in N,N-bis-(1-methylethyl)aminoethylamine (4.49 g, 0.0267 mole) is heated at 100° C. for 18 hours. The solution is concentrated at reduced pressure to an oil. The oil is dissolved in 2-propanol and the solution is treated with a saturated solution of hydrogen chloride in 2-propanol. The solution is diluted with anhydrous diethyl ether and allowed to crystallize. The crystals are filtered. Recrystallization from acetonitrile-diethyl ether yields pure 5-n-butyloctahydro-2-oxo-1H-indole-acetamide N-[bis[1-methylethyl]amino]ethyl]-·hydrochloride (3α, 7aα) with mp 116°-118° C.

The preferred compounds are those of Formula VII when x is hydrogen, methyl, ethyl, or n-butyl wherein R is H, $CH_{2n}N(CH_3)_2$, $(CH_2)_n[CH(CH_3)_2]_2$,

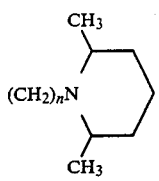

Particularly valuable compounds falling within the scope of the present invention include the following compounds and their stereoisomers:

cis-hexahydro-2-oxo-cyclopenta[b]pyrrole-1(2H)-acetamide;
cis-hexahydro-2-oxo-cyclohexa[b]pyrrol-1(2H)-acetamide;
cis-octahydro-2-oxo-1H-indole-1-acetic acid amide N-(2-bis[1-methylethyl]amino)ethyl;
cis-octahydro-2-oxo-cyclohepta[b]pyrrole-1(2H)-acetamide;
cis-octahydro-2-oxo-cyclohepta[b]pyrrole-1(2H)acetamide N-2-(dimethylamino)ethyl;
cis-decahydro-2-oxo-1H-cycloocta[b]pyrrole-1-acetamide5-n-butyloctahydro-2-oxo-1H-indole-acetamide (3α, 7aα); and
5-n-butyloctahyiro-2-oxo-1H-indole-acetamide N-2--[bis[1-methylethyl]amino]ethyl·hydrochloride (3α, 7aα), and the pharmaceutically acceptable acid addition salts thereof The compounds of the present invention are useful for treating senility or for reversing amnesia.

The effectiveness of the aforementioned compounds is determined by a test designed to show a compound's ability to reverse amnesia produced by electroconvulsive shock. The test is fully described in U.S. Pat. No. 4,145,347, issued Mar. 20, 1979, and is herein incorporated by reference. The only differences being that the test compounds in the present instance are administered orally and the length of the electroconvulsive shock is 1.0 seconds in duration.

The following criteria are used in interpreting the percent of amnesia reversal scores: 40% or more (active=A), 25–39% (borderline=C), and 0–24% (inactive=N).

Table 1 below reports the percent of amnesia reversal of orally administered:

cis-hexahydro-2-oxo-cyclopenta[b]pyrrole-1(2H)-acetamide;
cis-hexahydro-2-oxo-cyclohexa[b]pyrrol-1(2H)-acetamide;
trans-hexahydro-2-oxo-cyclohexa[b]pyrrol-1(2H)-acetamide;
cis-octahydro-2-oxo-1H-indole-1-acetic acid amide N-(2-bis[1-methylethyl]amino)ethyl·hydrochloride;
cis-octahydro-2-oxo-1H-indole-1-acetic acid amide N-2-(dimethylamino)ethyl·hydrochloride;
cis-octahydro-2-oxo-cyclohepta[b]pyrrole-1(2H)-acetamide;
cis-octahydro-2-oxo-cyclohepta[b]pyrrole-1(2H)-acetamide-N-2-(dimethylamino)ethyl;
cis-decahydro-2-oxo-1H-cycloocta[b]pyrrole-1-acetamide
5-n-butyloctahydro-2-oxo-1H-indole-acetamide (3α, 7aα);
5-n-butyloctahydro-2-oxo-1H-indole-acetamide N-2-[bis[1-methylethyl]amino]ethyl·hydrochloride (3α, 7aα).

TABLE I

| n | R | Amnesia Reversal | mg/kg 80 | 20 | 5 |
|---|---|---|---|---|---|
| 1 | H | | 50(A) | 50(A) | 37(C) |
| 2 | H | | 100(A) | 85(A) | 77(A) |
| | | * | 45(A) | 36(C) | 0(N) |
| 2 | H (5-n-butyl) | | 67(A) | 83(A) | 83(A) |
| 2 | $(CH_2)_2N[CH(CH_3)_2]$ (5-n-butyl) | | 27(C) | 40(A) | 33(C) |
| 2 | $(CH_2)_2N[CH(CH_3)_2]_2$ | | 24(N) | 20(N) | 40(A) |
| 2 | $(CH_2)_2N(CH_3)_2$ | | 36(C) | 67(A) | 50(A) |
| | | * | 25(C) | 42(A) | 31(C) |
| 3 | H | | 0(N) | 75(A) | 0(N) |
| 3 | $(CH_2)_2N(CH_3)_2$ | | 0(N) | 11(N) | 44(A) |
| 4 | H | | 45(A) | 45(A) | 35(C) |

*Replication. These results are within the experimental variation in the test.

The compounds of the present invention include solvates and hydrates and pharmaceutically acceptable salts of the basic compounds of the present invention.

The term pharmaceutically acceptable salt is intended to mean a relatively nontoxic acid addition salt, either from inorganic or organic acids such as, for example, hydrochloric, sulfuric, phosphoric, acetic, citric, oxalic, malonic, salicyclic, malic, gluconics, fumaric, succinic, ascorbic, maleic, methanesulfonic, and the like. The alkyl groups of the present invention comprise both straight and branched carbon chains of from one to about six carbon atoms. Representatives of such groups are methyl, ethyl, isopropyl, 3-methyl, pentyl, and the like.

In addition, the stereochemistry of the ring junctures between the fused rings may be either cis or trans. This latter possibility for geometrical isomerism is limited to some extent by the difficulty of forming trans-ring junctures in fused-ring systems involving five-membered lactam rings. For example, it is apparently not possible to synthesize structures in which a five-membered lactam ring is joined in a trans-configuration to another five-membered ring.

Further, for those compounds of the present invention in which the molecule has no plane of symmetry, steroisomerism is possible.

The present invention contemplates all possible ring-size variants, geometric isomers, and stereoisomers of the compounds depicted generically by structural Formula VII given above The terms "stereoisomers," "stereoisomerism," "optical isomerism," "optical isomers," "geometrical isomerism," and "geometrical isomers" as used through-out this specification and appended claims are those commonly employed by practitioners of the organic chemical art, specifically as defined on pages 1–6 of Eliel, "Stereochemistry of Carbon Compounds," McGraw-Hill, New York, 1962, incorporated herein by reference.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogenously therein by stirring. The molten homogeneous mixture is then poured into convenient sized molds, allowed to cool, and thereby solidify.

Liquid form preparations include solutions, suspensions, and emulsions. As an example may be mentioned water or water propylene glycol solutions for parenteral injection. Liquid preparations can also be formulated in solution in aqueous polyethyleneglycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such as used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatable therapeutic agents.

In therapeutic use as cognition activators, the mammalian dosage range for a 70 kg subject is from 1 to 1500 mg of body weight per day or preferably 25 to 750 mg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

Preparation of cis-hexahydro-2-oxo-cyclopenta[b]pyrrole-1(2H)-acetamide

A solution of cis-hexahydro-2-oxo-cyclopenta[b]pyrrole-1(2H)-acetic acid ethyl ester (3.25 g, 0.0154 mole) in methanol (200 ml) is saturated with anhydrous ammonia and stirred at ambient temperature 24 hours. The solution is concentrated at reduced pressure to yield a solid. Recrystallization from acetonitrile yields pure cis-hexahydro-2-oxo-cyclopenta[b]pyrrole-1(2H)-acetamide with a mp 142.5°–143.5° C.

EXAMPLE 2

Preparation of cis-hexahydro-2-oxo-cyclohexa[b]-pyrrol-1(2H)-acetamide

A solution of cis-octahydro-2-oxo-1H-indole-1acetic acid ethyl ester (15.43 g, 0.068 mole) in methanol (200 ml) is saturated with ammonia and stirred at ambient temperatures 24 hours. The solution is concentrated at reduced pressure to yield a solid. cis-Hexahydro-2-oxo-cyclopenta[b]pyrrole-1(2H)-acetamide with a mp 145°–145.5° C.

EXAMPLE 3

Preparation of trans-hexahydro-2-oxo-cyclohexa[b]-pyrrol-1(2H)-acetamide

A solution of trans-octahydro-2-oxo-1H-indole-1-acetic acid ethyl ester; (7.7 g, 0.032 mole) in methanol (200 ml) in methanol (200 ml) is saturated with ammonia and stirred at ambient temperatures 24 hours. The solution is concentrated at reduced pressure to yield a solid, trans-hexahydro-2-oxocyclohexa[b]pyrrol-1-(2H)-acetamide.

EXAMPLE 4

Preparation of cis-octahydro-2-oxo-1H-indole-1-acetic acid amide N-(2-bis[1-methylethyl]amino)ethyl-hydrochloride A solution of cis-octahydro-2-oxo-1H-indole-1-acetic acid ethyl ester (11.26 g, 0.05 mole) in N'-bis-(1-methylethyl)aminoethylamine (10.1 g, 0.0725 mole) is heated at 100° C. for 18 hours. The solution is concentrated at reduced pressure to yield an oil. The oil is chromatographed over silica gel (elution with dichloromethane and methanol, 92.5 and 7.5, respectively). The eluate is concentrated at reduced pressure to yield an oil. The oil is dissolved in 2-propanol and treated with a saturated solution of hydrogen chloride in 2-propanol. The solution is diluted with anhydrous diethyl ether to yield a solid.

Recrystallization from acetonitrile-anhydrous diethyl ether yields pure cis-octahydro-2-oxo-1H-indole-1-acetic acid amide N-(2-(bis[1-methylethyl]amino-hydrochloride with mp 160°–162° C.

EXAMPLE 5

Preparation of cis-octahydro-2-oxo-1H-indole-1-acetic acid amide N-2-(cis-2,6-dimethyl-1-piperidinyl)ethyl A solution of cis-octahydro-2-oxo-1H-indole-1-acetic acid ethyl ester (11.26 g, 0.05 mole) in N-2-(cis-2,6-dimethyl-1-piperidinyl)ethylamine (15.6 g, 0.1 mole) is heated at 100° C. for 18 hours. The solution is concentrated at reduced pressure to yield an oil. The oil is chromatographed over silica gel (elution with dichloromethane and methanol, 92.5 and 7.5, respectively). The eluate is concentrated at reduced pressure to yield an oil. The oil is distilled to yield pure cis-octahydro-2-oxo-1H-indole-1-acetic acid amide N-2-(cis-2,6-dimethyl-1-piperindinyl)ethyl-.

EXAMPLE 6

Preparation of cis-octahydro-2-oxo-1H-indole-1-acetic acid amide N-3-(cis-2,6-dimethyl-1-piperindinyl)propyl A solution of cis-octahydro-2-oxo-1H-indole-1-acetic acid ethyl ester (11.26 g, 0.05 mole) in N-3-(cis-2,6-dimethyl-1-piperindinyl)propylamine (17.0 g, 0.1 mole) is heated at 100° C. for 18 hours. The solution is concentrated at reduced pressure to yield an oil. The oil is chromatographed over silica gel (elution with dichloromethane and methanol, 92.5 and 7.5, respectively). The eluate is concentrated at reduced pressure to yield an oil. The oil is distilled to yield pure cis-octahydro-2-oxo-1H-indole-1-acetic acid amide N-3-(cis-2,6-dimethyl-1-piperidinylpropyl).

EXAMPLE 7

Preparation of cis-octahydro-2-oxo-1H-indole-1-acetic acid amide N-(2-dimethylaminoethyl)-hydrochloride A solution of cis-octahydro-2-oxo-1H-indole-1-acetic acid ethyl ester (13.52 g, 0.06 mole) in N,N-dimethylaminoethylamine (7.93 g, 0.09 mole) is heated at 100° C. for 18 hours. The solution is concentrated at reduced pressure to yield an oil. The oil is chromatographed over silica gel (elution with dichloromethane and methanol, 92.5 and 7.5, respectively). The eluate is concentrated at reduced pressure to yield an oil. The oil is dissolved in 2-propanol and treated with a saturated solution of hydrogen chloride in 2-propanol. The solution is diluted with anhydrous diethyl ether to yield a solid.

Recrystallization from acetonitrile-anhydrous diethyl ether yields pure cis-octahydro-2-oxo-1H-indole-1-acetic acid amide N-2-(dimethylaminoethyl)·hydrochloride, 0.5 $H_2O$ with mp 127°–130° C.

EXAMPLE 8

Preparation of cis-octahydro-2-oxo-cyclohepta[b]pyrrole-1(2H)-acetamide

A solution of cis-octahydro-2-oxo-cyclohepta[b]pyrrole-1(2H)-acetic acid ethyl ester (3.0 g, 0.0125 mole) in methanol (50 ml) is saturated with anhydrous ammonia. The solution is stirred at ambient temperature for 72 hours. the solution is concentrated at reduced pressure to yield a solid. Trituration with anhydrous diethyl ether yields pure cis-octahydro-2-oxo-cyclohepta[b]pyrrole-1(2H)acetamide with mp 140°–142° C.

EXAMPLE 9

Preparation of cis-octahydro-2-oxo-cyclohepta[b]pyrrole-1(2H)-acetamide N-2-(dimethylaminoethyl)

A solution of cis-octahydro-2-oxo-cyclohepta[b]pyrrole-1(2H)-acetic acid ethyl ester (4.35 g, 0.018 mole) in N,N-dimethylaminoethylamine (10 g, 0.113 mole) is heated at reduced pressure and distilled to yield pure cis-octahydro-2-oxo-cyclohepta[b]pyrrole-1(2H)-acetamide N-2-(dimethylaminoethyl) with mp 155°–160° C. at 0.1 mm.

EXAMPLE 10

Preparation of cis-decahydro-2-oxo-1H-cycloocta[b]pyrrole-1-acetamide

A solution of cis-decahydro-2-oxo-1H-cycloocta[b]pyrrole-1-acetic acid ethyl ester (4.0 g, 0.0157 mole) in methanol (30 ml) is saturated with anhydrous ammonia. The solution is stirred 18 hours. The solution is concentrated at reduced pressure to yield a solid. Trituration with anhydrous diethyl ether yields pure cis-decahydro-2-oxo-1H-cycloocta[b]pyrrole-1-acetamide with mp 110°–112° C.

EXAMPLE 11

Preparation of 5-n-butyloctahydro-2-oxo-1H-indole-acetamide (3aα, 7aα)

A solution of 5-n-butyloctahydro-2-oxo-1H-indole-acetic acid ethyl ester (3aα, 7aα) (5.0 g, 0.0179 mole) in methanol (50 ml) is saturated with anhydrous ammonia and stirred 18 hours at ambient temperature. The solution is concentrated at reduced pressure to yield a solid. Recrystallization from acetonitrile yields pure 5-n-butyloctahydro-2-oxo-1H-indole-acetamide (3aα, 7aα) with mp 148°–149° C.

EXAMPLE 12

Preparation of 5-n-butyloctahydro-2-oxo-1H-indole-acetamide N,N-[bis[1-methylethyl]amino]ethyl]-hydrochloride (3aα, 7aα)

A solution of 5-n-butyloctahydro-2-oxo-1H-indole-acetic acid ethyl ester (3aα, 7aα) (5.0 g, 0.0178 mole) in N,N-bis-(1-methylethyl)aminoethylamine (4.49 g, 0.0267 mole) is heated at 100° C. for 18 hours. The solution is concentrated at reduced pressure to an oil. The oil is dissolved in 2-propanol and the solution is treated with a saturated solution of hydrogen chloride in 2-propanol. The solution is diluted with anhydrous diethyl ether and allowed to crystallize. The crystals are filtered. Recrystallization from acetonitrile-diethyl ether yields pure 5-n-butyloctahydro-2-oxo-1H-indole-acetamide N,N-[bis[1-methylethyl]amino]ethyl]-hydrochloride (3aα, 7aα) with mp 116°–118° C.

We claim:

1. A compound having the structural formula

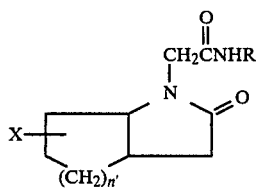

wherein n' is one, two, three, or four; X is H or a straight or branched alkyl of from one to four carbon atoms; R is H or $(CH_2)_nN(R'R'')$ in which n is two or three, R' and R'' are each independently hydrogen, a straight or branched alkyl of from one to six carbon atoms or combined with the nitrogen to which they are attached form a five to seven-membered ring which may optionally be substituted with one or more alkyl groups of from one to four carbon atoms; or a pharmaceutically acceptable acid addition salt thereof.

2. A compound according to claim 1 wherein R' and R'' are each independently hydrogen or a straight or branched alkyl of from one to six carbon atoms or combined with the nitrogen to which they are attached form a 1-pyrrolidinyl or 1-piperidinyl ring optionally substituted with one or more alkyl groups of from one to four carbon atoms, or a pharmaceutically acceptable acid addition salt thereof.

3. A compound according to claim 1 wherein n' is one.

4. A compound according to claim 1 wherein n' is two.

5. A compound according to claim 1 wherein n' is three.

6. A compound according to claim 1 wherein n' is four.

7. A compound according to claim 1 wherein R is hydrogen.

8. A compound according to claim 2 wherein R is $(CH_2)_nN(R'R'')$.

9. A compound according to claim 8 wherein R' and R'' are $CH_3$.

10. A compound according to claim 8 wherein R' and R'' are $C_2H_5$.

11. A compound according to claim 8 wherein R' and R'' are $CH(CH_3)_2$.

12. A compound according to claim 8 wherein R' and R'' when taken together with nitrogen are —(CH$_3$)—CH(CH$_2$)$_3$CH(CH$_3$)—.

13. A compound according to claim 8 wherein n is two.

14. A compound according to claim 8 wherein n is three.

15. A compound according to claim 1 wherein X is H or a straight or branched alkyl of from one to four carbon atoms.

16. A compound according to claim 1 and being cis-hexahydro-2-oxo-cyclopenta[b]pyrrole-1(2H)-acetamide.

17. A compound according to claim 1 and being cis-hexahydro-2-oxo-cyclohexa[b]pyrrol-1(2H)-acetamide.

18. A compound according to claim 1 and being trans-hexahydro-2-oxo-cyclohexa-[b]pyrrol-1(2H)-acetamide.

19. A compound according to claim 1 and being cis-octahydro-2-oxo-1H-indole-1-acetic acid amide N-2-(dimethylamino)ethyl-hydrochloride.

20. A compound according to claim 1 and being cis-octahydro-2-oxo-cyclohepta[b]pyrrole-1(2H)-acetamide.

21. A compound according to claim 1 and being cis-octahydro-2-oxo-cyclohepta[b]pyrrole-1(2H)-acetamide N-2-(dimethylamino)ethyl.

22. A compound according to claim 1 and being cis-decahydro-2-oxo-1H-cycloocta[b]pyrrole-1-acetamide.

23. A compound according to claim 1 and being 5-n-butyloctahydro-2-oxo-1H-indole-acetamide.

24. A compound according to claim 1 and being 5-n-butyloctahydro-2-oxo-1H-indoleacetamide N-2 [bis[1-methylethyl]amino]ethyl-hydrochloride.

25. A method of preparing a compound according to claim 1 which comprises:
  (a) reacting a 2-carboalkoxycycloalkanone with an alkali metal hydride and an alkyl α-haloacetate to form a 2-carboalkoxy-2-carboalkoxymethyl-cycloalkanone;
  (b) reacting the 2-carboalkoxy-2-carboalkoxymethyl cycloalkanone with acid to form the corresponding cycloalkanone-2-acetic acid;
  (c) reacting the cycloalkanone-2-acetic acid with an alcohol with an acid catalyst and heat to form the corresponding cycloalkanone-2-acetic acid alkyl ester;
  (d) treating the cycloalkanone-2-acetic acid alkyl ester with 0-methyldroxyamine·hydrochloride to form the corresponding cycloalkanone-2-acetic acid alkyl ester O-methyloxime;
  (e) hydrogenating the cycloalkanone-2-acetic acid alkyl ester O-methyloxime in the presence of a catalyst to form the corresponding 2-oxo-cycloalkyl[b]pyrrole;
  (f) reacting the 2-oxo-cycloalkyl[b]pyrrole with an alkali metal hydride and an alkyl-α-haloacetate to form the corresponding 2-oxocycloalkyl[b]pyrrole acetic acid alkyl ester;
  (g) reacting the 2-oxo-cycloalkyl[b]pyrrole acetic acid alkyl ester with ammonia or a primary amine to form a saturated cycloalkyl[b]pyrrole acetic acid amide, and, if desired, converting the basic compound to a pharmaceutically acceptable acid addition salt.

26. A method of preparing a compound according to claim 1 which comprises:

(a) reacting a para-alkylglyoxylanilide with an acid to produce the corresponding 5-alkyl-2,3-dioxoindole;
(b) hydrogenating catalytically the 5-alkyl-2,3-dioxoindole to form 5-alkyl-2-oxoindole;
(c) treating the 5-alkyl-2-oxo-indole with an alkali metal hydride and an alkyl α-haloacetate to form 5-alkyl-2-oxo-indole acetic acid ester;
(d) treating 5-alkyl-2-oxo-indole acetic acid ester with ammonia or a primary amine to form 5-alkyl-2-oxo-indole-acetic acid amide and, if desired, converting the basic product to a pharmaceutically acceptable acid addition salt.

27. An amnesia reversing pharmaceutical composition comprising an effective amount of a compound as defined in claim 1 in combination with a pharmaceutically acceptable carrier.

28. A method of reversing amnesia produced by electroconvulsive shock in mammals which comprises administering to said mammal an effective amount of a pharmaceutical composition in accordance with claim 27.

* * * * *